United States Patent [19]

Kaiser et al.

[11] Patent Number: 4,948,781
[45] Date of Patent: * Aug. 14, 1990

[54] NOVEL ODORANT AND/OR FLAVORING SUBSTANCES

[75] Inventors: Roman Kaiser, Uster; Dietmar Lamparsky, Wangen, both of Switzerland

[73] Assignee: Givaudan Corporation, Clifton, N.J.

[ * ] Notice: The portion of the term of this patent subsequent to Nov. 13, 2001 has been disclaimed.

[21] Appl. No.: 461,080

[22] Filed: Jan. 26, 1983

[30] Foreign Application Priority Data

Jan. 27, 1982 [CH] Switzerland ............................ 492/82

[51] Int. Cl.$^5$ .......................... A61K 7/46; C07C 43/15
[52] U.S. Cl. ........................................ 512/25; 131/276; 424/49; 424/65; 424/69; 424/70; 424/76.4; 252/174.11; 426/534; 568/596; 568/673; 568/687
[58] Field of Search .................. 568/673, 687, 596; 252/522 R; 426/534; 131/276; 512/25

[56] References Cited

U.S. PATENT DOCUMENTS 3,784,609  1/1974  Neale ............................... 568/687 X
3,920,752  11/1975  Lamparsky ..................... 260/601 R
4,122,291  10/1978  Kyo et al. ............................ 568/887

FOREIGN PATENT DOCUMENTS 0045453  2/1982  European Pat. Off. .

OTHER PUBLICATIONS

Arctander, *Perfume and Flavor Chemicals*, vol. II, Monographs 1960 and 1961 (1969).
Bjelouss, Ber., vol. 43 (1910), 2330–2333.

*Primary Examiner*—Charles F. Warren
*Attorney, Agent, or Firm*—Robert F. Tavares; Linda A. Vag

[57] ABSTRACT

The invention is concerned with compounds of the formula:

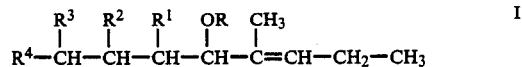

wherein:
R represents an alkyl group of one to four carbons, an alkenyl group of two to four carbons or a 1-alkoxyalkyl group of the formula

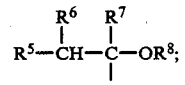

$R^1$, $R^2$ and $R^3$ may be the same or different and represent hydrogen, methyl or ethyl;
$R^4$ represents hydrogen, an alkyl group of from one to five carbon atoms, an alkenyl group of from two to four carbon atoms or an alkylidene group of from one to four carbon atoms;
$R^5$, $R^6$ and $R^7$ may be the same or different and represent hydrogen, methyl or ethyl with the proviso that the sum $R^5+R^6+R^7$ does not exceed two carbon atoms; and
$R^8$ represents methyl or ethyl;
with the proviso that at least two, but not more than three of the symbols $R^1$, $R^2$, $R^3$ and $R^4$ represent hydrogen.

This invention is also concerned with odorant and flavoring compositions containing these compounds.

29 Claims, No Drawings

NOVEL ODORANT AND/OR FLAVORING SUBSTANCES

THE INVENTION

The invention is concerned with novel compounds of the formula:

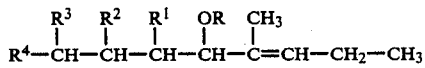    I wherein

R represents an alkyl group of one to four carbons, an alkenyl group of two to four carbons or a 1-alkoxy-alkyl group of the formula

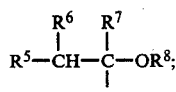

$R^1, R^2$ and $R^3$ may be the same or different and represent hydrogen, methyl or ethyl;
$R^4$ represents hydrogen, an alkyl group of from one to five carbon atoms, an alkenyl group of from two to four carbon atoms or an alkylidene group of from one to four carbon atoms;
$R^5$, $R^6$ and $R^7$ may be the same or different and represent hydrogen, methyl or ethyl with the proviso that the sum $R^5+R^7$ does not exceed two carbon atoms; and $R^8$ represents methyl or ethyl;
with the proviso that at least two, but not more than three of the symbols $R^1, R^2, R^3$ and $R^4$ represent hydrogen.

The invention is also concerned with odorant and flavoring compositions containing the compounds of formula I and methods for making same.

DESCRIPTION OF THE PREFERRED EMBODIMENTS

The novel compounds represented by formula I are useful as odorants and flavorants.

Formula I embraces a number of ethers and mixed acetals. While R may be any of the groups as defined above, an alkyl group of from one to four carbon atoms is preferred with the methyl group being especially preferred.

Formula I also embraces mixed acetals which are essentially alkyl ethers wherein R is an alkyl group of from two to four carbons which is substituted with a methoxy or ethoxy group at the 1'-position, with the ethoxy-ethyl group, i.e. wherein $R^8$ is ethyl and $R^5$, $R^6$ and $R^7$ are hydrogen, being especially preferred. In such mixed acetals it is also preferred that the radical

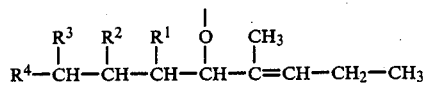    I have from ten to fourteen carbon atoms.

The groups $R^1, R^2$ and $R^3$ are as defined with hydrogen being preferred for $R^1$ and $R^2$ and hydrogen or methyl being preferred for $R^3$. While $R^4$ can be any of the groups defined, $R^4$ representing an alkyl group of from one to five carbon atoms (e.g. methyl, ethyl, propyl, isopropyl, butyl, isobutyl, amyl, isoamyl) is preferred with methyl or ethyl being especially preferred.

In those compounds wherein R represents alkenyl groups of from two to four carbons (e.g. vinyl, propylene, allyl, methallyl, butylene), vinyl and allyl groups are preferred.

In those compounds wherein $R^4$ is an alkenyl group of from two to four carbons (e.g. vinyl, allyl, methallyl, 3'-butenyl, 2'-methyl-1'-propenyl), the vinyl group is preferred. When $R^4$ is an alkylidene group of from one to four carbons (e.g. methylidene, ethylidene, propylidene, isopropylidene, butylidene), the methylidene group is preferred.

Formula I is intended to embrace all possible stereoisomers including cis or trans configuration at the double bonds.

The invention is also concerned with a process for the manufacture of the compounds of formula I. This process is characterized by etherifying an alcohol of the formula

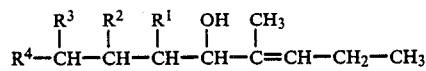    II wherein $R^1, R^2, R^3$ and $R^4$ are as previously defined.

The etherification can be carried out in a manner similar to those known in the art. For example, an alcoholate can first be prepared from the corresponding alcohol of formula II, and then alkylated or alkenylated. See, for example, Organikum, Organisch-chemisches Grundpraktikum, 9th Edition, VEB Deutscher Verlag der Wissenschaften, Berlin 1969, 222 et seq.

The alcoholoates are conveniently prepared by reacting the basic alcohols with an alkali metal such as, for example, sodium or potassium or an alkali metal hydride such as, for example, sodium hydride in an inert solvent such as benzene, toluene, xylene etc. These can then be alkylated with suitable alkylating agents, especially dialkyl sulphates and alkyl halides with alkyl bromides being especially preferred.

The alkoxy-alkyl derivatives of formula I (i.e. the mixed acetals) are conveniently manufactured by reacting an alcohol of formula II with an enol ether of the formula

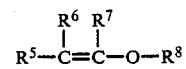    III wherein the symbols $R^5$, $R^6$, $R^7$ are the same or different and represent hydrogen, methyl or ethyl, with the proviso that the sum of carbon atoms in all three symbols ($R^5, R^6, R^7$) does not exceed two; and $R^8$ represents methyl or ethyl.

The reaction is conveniently carried out in the presence of catalytic amounts of a mineral acid (e.g. hydrochloric acid, sulphuric acid or phosphoric acid) or a strong organic acid such as, for example, p-toluenesulphonic acid (monohydrate). This addition of an alcohol to the double bond of an enol ether generally requires no additional solvent. The addition of an excess of the enol ether or the addition of an aprotic solvent (e.g. hexane, cyclohexane, etc.) may be desirable. The reaction normally proceeds smoothly at room temperature, but it can also be carried out at slightly higher or lower temperatures. A temperature range of 0°–80°0 C., would be most suitable with a temperature range of +10°0 C. to +40°0 C. being preferred.

The starting materials of formula II can be obtained by reacting 2-methyl-2-pentenal with a halide of the formula

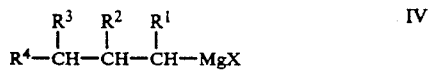

wherein $R^1, R^2, R^3$ and $R^4$ are as previously defined and X stands for halogen.

The halide of formula IV can be any halide, but the bromide is preferred.

The reaction of 2-methyl-2-pentenal with a halide of formula IV is conveniently carried out according to known methods for Grignard reactions; see, for example, Organikum, Org. chem. Grundpraktikum, reprint 15th Edition, VEB deutscher Verlag der Wissenschaften, Berlin 1977, 617 et seq. For example, the reaction is conveniently carried out in diethyl ether, a higher ether or tetrahydrofuran as solvent at temperatures of about 0°–80° C.

The starting material of formula II is usually obtained as an isomer mixture in which the trans form of the olefinic portion of the molecule (i.e. trans—CH(OH)—C(CH₃)=CH—CH₂—CH₃) largely predominates. It is more economical and therefore preferred to use this isomeric mixture.

The compounds of formula I have particular organoleptic properties which makes them especially suitable as odorant and/or flavouring substances and the invention is also concerned with their use as odorant and/or flavouring substances. Each of the compounds has its own unique characteristics. For example, 5-methoxy-4-methyl-3-decene has a very fresh, fruity odor reminiscent of apples, blueberries and other kinds of berry which is coupled with a green and herby odor. The isomeric 5-methoxy-2,6-dimethyl-6-nonene, on the other hand, has a very sweet-fruity, powdery odor, while the corresponding ethyl ether (5-ethoxy-2,6-dimethyl-6-nonene), however, is primarily reminiscent of alcoholic drinks (whisky) with additional flowery-spicy aspects. The 5-(1'-ethoxyethoxy)2,6-dimethyl-6-nonene exhibits green, flowery, slightly powdery and very sweet odor notes which are replaced in the isomeric 5-(1'-ethoxyethoxy)-4-methyl-3-decene by bitterish-green odor notes reminiscent of citrus coupled with chocolate-like odor notes.

In general the novel ethers of formula I are alkali stable and exhibit interesting, mainly fruity-green odor notes; the flowery, spicy and powdery nuances of which make them excellent odorant substances. They also have flavor notes reminiscent of various kinds of fruit and also of caramel and chocolate, which makes them valuable substances for flavoring foodstuffs.

On the basis of their natural odor notes the compounds of formula I are especially suitable for the modification of, for example:

(a) flowery compositions in which, for example, top notes are to be enhanced (e.g. for cologne types and the like as well as essences), (b) compositions of the chypre and fougere type in which fresh, herby, fruity-citrus like elements are to be accentuated, (c) tobacco and woody compositions wherein, for example, the patchouli component is advantageously enveloped and this modification also appears in the bottom note, and (d) compositions with green notes where, in particular, a desired rounding-off and harmonizing effect is provided.

The compounds of formula I combined with numerous known natural or synthetic ingredients of odorant and/or flavoring substance compositions, whereby the range of the natural ingredients can embrace not only readily-volatile but also semi-volatile and slightly-volatile components and the range of the synthetic ingredients can embrace representatives from almost all classes of substances, as will be evident from the following compilation:

Natural products:

Basil oil, tree moss absolute, mugwort oil, bergamot oil, cassis bud absolute, castoreum, cedarwood oil, Cistus labdanum, civet, coriander oil, oak moss, elemi oil, pineneedle oil, galbanum, geranium oil, jasmine absolute and its synthetic substitute, jonquille absolute, labdanum, lavender oil, mandarin oil, mastix absolute, palmarosa oil, patchouli oil, petitgrain oil Paraguay, sandalwood oil, thyme oil, frankincense ylang-ylang oil, lemon oil etc.

Alcohols: Citronellol, geraniol, cis-3-hexenol, linalool, terpineol, phenylethyl alcohol, rhodinol, Sandela ® (3-isocamphyl-5-cyclohexanol), Dimetol ® (2,6-dimethyl-heptan-2-ol), cinnamic alcohol synthetic and its substitute etc.

Aldehydes:

α-Amylcinnamaldehyde, cyclamen aldehyde, dodecanal, heliotropin, α-hexylcinnamaldehyde, hydroxycitronellal, 2,6,10-trimethyl-undec-9 en-1-al (Adoxal ™), decanal, undecanal, ω-undecylene aldehyde etc.

Ketones:

Isoraldeine ™ (isomethyl-α-ionone), α-ionone, β-ionone, 3-prenylisocaranone, acetylated cedarwood oil, p-methylacetophenone etc.

Esters:

Amyl salicylate, benzyl acetate, citronellyl acetate, bornyl acetate, terpenyl acetate, geranyl acetate, cis-3-hexenyl acetate, cis-3-hexenyl benzoate, 1-methyl-2-sec-butylcyclohexyl acetate, methyl dihydrojasmonate, phenoxyethyl isobutyrate, phenylethyl tiglate, cinnamyl acetate, styrallyl acetate, 2,3,6,6-tetramethylcyclohex-2-ene-carboxylic acid ethyl ester, 3,6,6-trimethyl-2-ethyl-cyclohex-2-ene-carboxylic acid ethyl ester, vetivenyl acetate, cedryl acetate, p-tert. butylcyclohexyl acetate etc.

Various:

Indole, coumarin, eugenol, isobutylquinoline, limonene, p-menthane-8-thiol-3-one, 1-methylcyclododecyl methyl ether, γ-nonalactone, δ-decalactone, γ-undecalactone, musk ambrette, Galaxolid ® (1,3,4,6,7,8-hexahydro-4,6,6,7,8,8-hexamethyl-cyclopenta-γ-2-benzopyran), musk ketone, Musk 174 ™ (12-oxahexadecanolide) etc.

The compounds of formula I can be used in compositions in wide limits which, for example, can extend from 0.1% in the case of detergents to 50% in the case of alcoholic solutions. It will be appreciated that these values are not limiting values, since the experienced perfumer can also achieve effects with even lower concentrations or can synthesize novel complexes with even higher concentrations (e.g. with up to 60%). The preferred concentrations range between 0.5% and 20%. The compositions produced with the compounds of formula I can be used for all kinds of perfumed consumer goods (eau de cologne, eau de toilette, essences, lotions, creams, shampoos, soaps, salves, powders., toothpastes, mouth washes, deodorants, detergents, tobacco etc).

The compounds of formula I can accordingly be used for the manufacture of compositions and, as will be evident from the foregoing compilation, a wide range of known odorant substances can be used. In the production of such compositions, the known odorant substances referred to earlier can be used according to methods which are known to the perfumer such as, for example, according to W. A. Poucher, Perfumes, Cosmetics and Soaps 2, 7th Edition, Chapman and Hall, London, 1974.

As flavouring substances the compounds of formula I can be used, for example, for producing, improving, intensifying, enhancing or modifying fruit flavours (e.g. melon, quince, peach and apricot, berry flavours or chocolate flavours in foodstuffs (yoghurt, confectionery etc) luxury consumables (tea, tobacco, etc. and drinks (alcoholic drinks, etc.).

The pronounced flavour qualities of the compounds of formula I enable them to be used in low concentrations A suitable concentration range is, for example, 0.01–100 ppm, preferably 0.1–20 ppm, in the finished product (i.e. the flavoured foodstuff, luxury consumable or drink).

In the flavouring of, for example, tobacco, the concentration can, however, also be higher and can have a wider range; for example, the range of 1–1000 ppm, preferably 50–500 ppm.

The compounds of formula I can be mixed with the ingredients used for flavouring substance compositions or can be added to such flavourants in the usual manner. Among the flavourants contemplated in accordance with the invention there are to be understood flavouring substance compositions which can be diluted or dispersed in edible materials in a manner known per se. They contain, for example, about 0.1–10 wt. %, especially 0.5–3 wt. % of formula I compounds. They can be converted according to methods known per se into the customary forms of use such as solutions, pastes or powders. The products can be spray-dried, vacuum-dried or lyophilized.

The known flavouring substances conveniently used in the production of such flavourants are either referred to in the foregoing compilation or can be readily concluded from the literature; see, for example, J. Merory, Food Flavourings, Composition, Manufacture and Use, Second Edition, The Avi Publishing Company, Inc., Westport, Conn. 1968, or G. Fenaroli, Fenaroli's Handbook of Flavour Ingredients, Second Edition, Volume 2, CRC Press, Inc. Cleveland, Ohio, 1975.

For the production of such customary forms of use there can be used, for example, the following carrier materials, thickening agents, flavour improvers, spices, auxilliary ingredients etc:

Gum arabic, tragacanth, salts or brewers' yeast, alginates, carrageen or similar absorbants; indoles, maltol, dienals, spice oleoresins, smoke flavors; cloves, diacetyl, sodium citrate; monosodium glutamate, disodium inosine-5'-monophosphate (IMP), disodium guanosine-5-phosphate (GMP); or special flavoring substances, water, ethanol, propylene glycol, glycerine.

ILLUSTRATION OF THE PREFERRED EMBODIMENTS

EXAMPLE 1

5.0 g of 4-methyl-3-decen-5-ol dissolved in 25 ml of toluene are added dropwise over a period of 30 minutes at 80° C. while stirring to 1.54 g of a 55–60% sodium hydride dispersion in 25 ml of toluene. The mixture is stirred at 80° C. for 12 hours, cooled to 40° C. and treated dropwise with 5.6 g of dimethyl sulphate, the temperature again rising to 80° C. In order to complete the reaction, the mixture is stirred at 80° C. for a further 3 hours. After cooling to 40° C., 10 ml of ethanol are added thereto. The mixture is heated to boiling for a short period and then treated with cold 2N sodium hydroxide. The product is taken up in hexane, washed neutral, chromatographed on 250 g of silica gel in order to remove the oil of the sodium hydride dispersion used and the thus-obtained crude product is fractionally distilled. There are obtained 4.1 g (76% of theory) of 5-methoxy-4-methyl-3-decene of boiling point 100°–105° C./14 Torr, $n_D^{20}=1.4337$. Odour: very fresh, fruity, green, apple-like, blueberries, blackberries, herbaceous.

IR: 1670, 1094, 854 cm$^{-1}$;

NMR: ~0.90 (2 overlapping t, GH); 1.52 (s, 3H); 3.18 (s,3H) 3.39 (t, 1H); 5.32 (t, LH);

MS: 184 (M$^+$, 1), 113(100), 81(39), 69(11), 55(17), 41(13).

The starting material can be prepared as follows:

2.4 g (0.1 g-atoms) of magnesium in 50 ml of absolute ether are placed in an apparatus which is usual for Grignard reactions. 15.0 g (0.1 mol) of n-amyl bromide in 50 ml of absolute ether are subsequently added dropwise while stirring and under a protective gas atmosphere (nitrogen) so that the ether constantly boils slightly after the reaction has started. After completion of the addition, the mixture is held at reflux temperature for a further 30 minutes, then cooled to 10° C. and a solution of 7.85 g (0.08.mol) of 2-methyl-2-pentenal in 20 ml of absolute ether is added dropwise thereto. In order to complete the reaction, the mixture is stirred at room temperature for a further 12 hours. After decomposing the Grignard complex with saturated ammonium chloride solution and ice, the supernatant ethereal solution is washed with saturated sodium chloride solution and subsequently dried. After evaporation of the solvent, there remain behind 13.6 g of crude product which are fractionally distilled. There are thus obtained 8.9 g of pure 4-methyl-3-decen-5-ol of boiling point 103° C./12 Torr, $n_D^{20}=1.4499$.

IR: 3340, 2958 +2924, 2888 +1858, 1670, 1460, 1024, 854 cm$^{-1}$;

NMR: (360 MHz): 0.89 (t, 3H); 0.965 (t, 3H); 1.595 (s, 3H); 2.03 (m, 2H); 3.96 (t, 1H); 5.36 (t, 3H);

MS: m/e=170 (M$^+$, 6), 155(1), 141(18), 128(2), 109(2), 99(100), 81(19), 71(15), 55(19), 43(42).

EXAMPLE 2

6.13 g of a 55-60% sodium hydride dispersion in 100 ml of benzene are placed in a reaction vessel equipped with stirrer, thermometer, reflux condenser and dropping funnel and a solution of 20.0 g of 2,6-dimethyl-6-nonen-5-ol in 100 ml of benzene is added dropwise thereto over a period of 30 minutes while stirring at room temperature. In order to complete the reaction, the mixture is held at reflux temperature for 12 hours. The mixture is subsequently cooled to 20° C. At this temperature there are gradually added dropwise 20.7 g of dimethyl sulphate so that the temperature does not exceed 35° C. (exothermic reaction). After completion of the addition, the mixture, which becomes thicker, is heated to reflux temperature for a further 4 hours, then cooled and treated with 25 ml of methanol. After 5 minutes, there is added dropwise a solution of 6.7 g of sodium hydroxide in 40 ml of water and the mixture is again heated to reflux temperature. After cooling, the product is taken up in ether, washed neutral with water and the solvent is distilled off over a Vigreux column. The crude product remaining behind is rectified under a water-jet vacuum with the addition of 0.1 g of sodium carbonate and yields 13.3 g (61.7% of theory) of pure 5-methoxy-2,6-dimethyl-6-nonene of boiling point 78° C./12 Torr, $n_D^{20}=1.4339$. Odour: sweet, fruity, powdery, green.

IR: 1670, 1384, 1368, 1094, 855 cm$^{-1}$;

NMR: ~0.90 (overlapping d and t, together 9H); 1.54 (s,3H); 3.18 (s, 3H); 3.39 (t, 1H); 5.32 (t, 1H);

MS: 184(M+, 1), 113(100), 81(38), 55(17), 41(12).

The starting material can be prepared as follows:

69.5 g (2.9 g-atoms) of magnesium are placed in 500 ml of absolute ether Subsequently, a solution of 438 g of isoamyl bromide, which contains about 1.5% of n-amyl bromide in accordance with gas chromatography, in 1.2 l of absolute ether is added dropwise so that the exothermic reaction keeps the ether constantly at the boiling point After completion of the addition, the mixture is held at reflux temperature for a further 30 minutes. The Grignard solution is then cooled to 10° C. 236.5 g (2.41.mol) of 2-methyl 2-pentenal in 600 ml of absolute ether are then added dropwise within 40 minutes, the temperature then lying permanently between 10° C. and 20° C. In order to complete the reaction, the mixture is held at reflux temperature for a further 1 hour. The mixture is subsequently added to ice, decomposed with aqueous hydrochloric acid, the ethereal solution is washed neutral with soda and saturated sodium chloride solution and thereupon dried. The crude product (480 g) remaining behind after distillation of the solvent is fractionally distilled over a Widmer column and gives 312 g of 2,6-dimethyl-6-nonen-5-ol (III) of boiling point 62° C./0.05 Torr, $n_D^{25}=1.4479$, which contains 1.5% of 4-methyl-3-decen-5-ol in accordance with gas chromatography (Carbowax, 130° C.).

IR: 3350, 2956 +2930, 2866, 1670, 1468, 1386, 1368, 1012, 856 cm$^{-1}$;

NMR: (60 MHz): 0.88+0.90 (converging, 9H); 1.59 (s, 3H); 2.02 (t, 2H); 3.93 (t, 1H); 5.33 (t, 1H);

MS: m/e=170(7), 141(16), 123(4), 99(100), 81(34), 71(19), 55(36), 43(91).

EXAMPLE 3

Analogously to Examples 1 and 2, from 4,6-dimethyl-3-nonen-5-ol and 4,7-dimethyl-3-nonen-5-ol respectively there are obtained in comparable yields the isomeric methyl ethers (a) 5-methoxy-4,6 dimethyl-3-nonene (boiling point 76° C./12 Torr, $n_D^{20}=1.4355$, odour: flowery,fruity, green, herbaceous, earthy, very diffusive), or (b) 5-methoxy-4,7-dimethyl-3-nonene (boiling point 70° C./12 Torr, $n_D^{20}=1.4354$, odour: herbaceous, earthy, green).

The starting materials for (a) and (b) can be prepared as follows:

(a) 28.3 g (1.18 g-atoms) of magnesium in 200 ml of ether are placed in an apparatus which is customary for Grignard reactions. 178.1 g (1.18 mol) of 2-bromopentane in 500 ml of absolute ether are subsequently added dropwise while stirring and under a protective gas atmosphere (nitrogen) so that the ether constantly boils slightly after the reaction has started. After completion of the addition, the mixture is held at reflux temperature for a further 30 minutes, then cooled to 10° C. and a solution of 96.1 g (0.98 mol) of 2-methyl-2-pentenal in 300 ml of ether is added dropwise during 30 minutes so that the temperature lies permanently between 10° C. and 20° C. In order to complete the reaction, the mixture is refluxed for a further 1 hour, then the Grignard complex is decomposed with saturated ammonium chloride solution and ice, the supernatant etherial solution is washed with saturated sodium chloride solution and subsequently dried. After evaporation of the solvent, there remain behind 176 g of crude product which are fractionally distilled There are thus obtained 119 g (71.4%) of olfactorily good 4,6-dimethyl-3-nonen-5-ol of boiling point 92° C./12 Torr.

IR: 3380, 2958, 2924, 2865, 1670, 1460, 1378, 1300, 1005, 854;

NMR: 0.70 - 1.20 (2t and 1d, mutually overlapping, 9H); 1.58 (s, 3H); 2.02 (m, 2H); 3.67 (m, 1H); 5.34 (t, J~6.5, 1H);

MS: 170 (M+, 2), 141(2), 128(3), 123(1), 109(1), 99(100), 81(25), 71(12), 55(11), 43(72).

(b) The Grignard reagent obtained by reacting 11.8 g (0.49 g-atoms) of magnesium in 50 ml of ether with 67.13 g (0.49 mol) of isobutyl bromide in 250 ml of ether is reacted with 40.0 g (0.41 mol) of 2-methyl-2-pentenal in 100 ml of ether. The fractional distillation of the crude product (94 g) over a 20 cm Widmer column gives 44.4 g (69.4%) of olfactorily good 4,7-dimethyl-3-octen-5-ol of boiling point 47°-48° C./0.04 Torr.

IR: 3350, 2958, 2930, 2865, 1670, 1468, 1383, 1367, 1305, 1050, 1000, 856;

NMR: 0.80-1.20 (1d+1t, 9H); 1.60 (s, 3H); 2.02 (m, 2H); 4.08 (t, J~6.5, 1H); 5.37 (t, J~6.5, 1H);

MS: 156 (M+, 9), 127(24),114(16), 109(6), 99(100).

EXAMPLE 4

Analogously to Examples 1 to 3, from 4,6-dimethyl-3-octen-5-ol there is obtained 5-methoxy-4,6-dimethyl-4-octene, boiling point 65°/12 Torr, $n_D^{20}=1.4329$, odour: very green, reminiscent of plant stalks.

The starting material can be prepared as follows:

The Grignard reagent obtained by reacting 18.7 g (0.77 g-atom) of magnesium in 100 ml of ether with 105.4 g (0.77 mol) of 2-bromobutane in 300 ml of ether is reacted with 62.72 g (0.64 mol) of 2-methyl-2-pentenal in 200 ml of ether. The fractional distillation of the crude product (98.8 g) over a 20 cm Widmer column gives 68.4 g (68.5%) of olfactorily good 4,6-dimethyl-3-octen-5-ol of boiling point 83° C./12 Torr.

IR: 3400, 2960, 2930., 2870, 1670, 1460, 1378, 1300, 1035, 1000, 858;

NMR: 0.70 - 1.10 (2t +1d, mutually overlapping 9H); 1.58 (s, 3H); 2.02 (m, 2H); 3.68 (m, 1H); 5.37 (t, J~6.5, 1H);

MS: 156 (M+, 1), 109(1), 99(54), 81(20), 71(10), 57(12), 55(15), 43(100), 41(22), 39(7).

EXAMPLE 5

Analogously to Example 2, from 20.0 g of 2,6-dimethyl-6-nonen-5-ol and 25.3 g of diethyl sulphate there are obtained 10.9 g of ,5-ethoxy-2,6-dimethyl-6-nonene, boiling point 85° C./12 Torr, $n_D^{20}=1.4315$, odour: whisky-like, green, fruity, flowery, spicy.

IR: 1670, 1386, 1368, 1116, 1086, 855 cm$^{-1}$;

MS: 198 (M+, 1), 127(100), 99(39), 81(27), 71(10), 55(17), 43(55).

EXAMPLE 6

Analogously to Examples 1 and 5, from 20 g of 4-methyl-3-decen-5-ol and 27.1 g of diethyl sulphate there are obtained 18.6 g of 5-ethoxy-4-methyl-3-decene of boiling point 37° C./0.03 Torr, $n_D^{20}=1.4330$. Odour: fatty, green berry-like.

EXAMPLE 7

20 g of 4-methyl-3-decen-5-ol dissolved in 100 ml of toluene are added dropwise at 80° C. over a period of 30 minutes to 6.2 g of a 55-60% sodium hydride dispersion in 100 ml of toluene. The mixture is stirred at 80° C. for 12 hours, then cooled to 50° C. and treated dropwise with a solution of 24.1 g of n-butyl bromide in 50 ml of toluene. The mixture is subsequently held at reflux temperature for 6 hours. For the working-up, the mixture is treated at room temperature with water, the organic layer is separated and washed neutral with water, dried and, after the addition of 0.2 g of potassium carbonate, fractionally distilled There are obtained 20.7 g of 5-butoxy-4 methyl-3-decene of boiling point 60° C./0.03 Torr, $n_D^{20}=1.4378$. Odour: caramel-like, delicate, fatty-fruity.

IR: 1670, 1094 cm$^{-1}$;

MS: 226(M+, 1), 155(66), 99(100), 81(18), 71(7), 55(13), 43(36).

The starting material can be prepared as follows:

2.4 g (0.1 g-atoms) of magnesium in 50 ml of absolute ether are placed in an apparatus which is customary for Grignard reactions. 15.0 g (0.1 mol) of n-amyl bromide in 50 ml of absolute ether are subsequently added dropwise while stirring and under a protective gas atmosphere (nitrogen) so that the ether constantly boils slightly after the reaction has started. After completion of the addition, the mixture is held at reflux temperature for a further 30 minutes, then cooled to 10° C. and a solution of 7.85 g (0.08 mol) of 2-methyl-2 pentenal in 20 ml of absolute ether is added dropwise thereto. In order to complete the reaction, the mixture is stirred at reflux temperature for a further 12 hours. After decomposing the Grignard complex with saturated ammonium chloride solution and ice, the supernatant etherial solution is washed with saturated sodium chloride solution and subsequently dried. After evaporation of the solvent, there remain behind 13.6 g of crude product which are fractionally distilled. There are thus obtained 8.9 g of pure 4 methyl-3-decen-5-ol of boiling point 103° C./12 Torr, $n_D^{20}=1.4499$.

IR: 3340, 2958 +2924, 2888 +1858, 1670, 1460, 1024, 854 cm$^{-1}$;

NMR: (360 MHz): 0.89 (t, 3H); 0.965 (t, 3H); 1.595 (s, 3H); 2.03 (m, 2H); 3.96 (t, 1H); 5.36 (t, 3H); MS: m/e=170 (M+, 6), 155(1), 141(18), 128(2), 109(2), 99(100), 81(19), 71(15), 55(19), 43(42).

EXAMPLE 8

10 g of 4-methyl-3-decen-5-ol are reacted with 12.1 g of allyl bromide analogously to Example 7. After the usual working-up, there are obtained 6.9 g of 5-allyloxy-4-methyl-3-decene, boiling point 51° C./0.03 Torr, $n_D^{20}=1.4447$, odour: fatty, fruity, green, quince.

IR: 1670, 1646, 1090, 998, 924, 860 cm$^{-1}$;

MS: 210 (M+, 1), 139(100), 97(77), 69(32), 41(74).

EXAMPLE 9

10.0 g of 2,6-dimethyl-6-nonen-5-ol and 12.7 g of ethyl vinyl ether are placed in a reaction vessel and treated cautiously while stirring with 0.1 ml of concentrated hydrochloric acid. The mixture warms slightly; it is stirred at room temperature for 24 hours and then taken up in hexane The hexane solution is washed neutral with aqueous sodium hydrogen carbonate solution and water, dried and fractionally distilled in a water-jet vacuum. There are thus obtained 8.3 g (58.3% of theory) of 5-[1'-ethoxyethoxy]-2,6-dimethyl-6-nonene of boiling point 110° C./12 Torr, $n_D^{20}=1.4340$. In the gas-chromatographical analysis there appears a double peak in the ratio 1:1 corresponding to the two asymmetric carbon atoms in the molecule Odour: green, flowery, sweet, powdery.

IR: 1670, 1124, 1096, 1058, 1012, 960 cm$^{-1}$;

NMR: (360 MHz): 0.87 (d,6H); 0.96 (t,3H); 1.20 (t,3H); 1.26 (t,3H); 1.59 (s,3H); 2.04 (m,2H); 2.85-3.70 (m, total 3H); 4.59 (m, 1H); 5.31 (m,1H);

MS: 171, 97, 81, 73(100), 55, 45.

EXAMPLE 10

10.0 g of 4-methyl-3-decen-5-ol and 12.7 g of ethyl vinyl ether are reacted analogously to Example 9 to give 9.7 g of 5-[1'-ethoxyethoxy]-4-methyl-3-decene, boiling point 115° C./12 Torr, $n_D^{20}=1.4349$, odour: green, bitterish, citrus-like, reminiscent of chocolate.

EXAMPLE 11

10 g of 2,6-dimethyl-6-nonen-5-ol and 12 7 g of isopropenyl methyl ether are mixed and treated with 3 drops of concentrated hydrochloric acid. The mixture is subsequently held at reflux temperature for 15 hours, cooled, taken up in hexane and washed neutral with sodium hydrogen carbonate solution and water. After distillation of the solvent, there are obtained 14.1 g of crude 5-[1'-methoxy-1'-methyl-ethoxy]-2,6-dimethyl-6-nonene which are rectified in a water-jet pump vacuum (boiling point 109° C./12 Torr, $n_D^{20}=1.4379$). The mixed acetal decomposes when subjected to gas chromatography and must therefore be tested for purity by thin-layer chromatography (elution agent: hexane/pentane/chloroform/ethyl acetate in the ratio 25:25:50:5); $R_f=0.60$.

IR: 1664, 1384, 1374, 1218, 1082, 1024 cm$^{-1}$;

NMR: (360 MHz): δ=0.85 (d,3H); 0.87 (d,3H); 0.94 (t, 3H); 1.30 (s,3H); 1.33 (s,3H); 1.50 (m,4H); 1.56 (s,3H); 2.02 (m,2H); 3.18 (s,3H); 3.97 (t, 1H); 5.28 (t,1H);

MS: 212 (M-CH$_2$O). 153. 109, 97, 81, 73(100), 55, 43.

EXAMPLE 12

Analogously to Example 11, from 10 g of 4-methyl-3-decen-5-ol there are obtained 8.8 g of 5-[1'-methoxy-1'-methyl-ethoxy]-4-methyl-3-decene of boiling point 111° C./12 Torr, $n_D^{20}=1.4391$, odour: fatty, citrus-like, soapy.

EXAMPLE 13

20.0 g (0.11 mol) of 4-methyl-3 undecen-5-ol dissolved in 35 ml of toluene are added dropwise while stirring over a period of 30 minutes to 5.90 g (about 0.14 mol) of a 55-60% sodium hydride dispersion in 100 ml of toluene. The mixture is stirred at reflux temperature for 12 hours, then cooled to 40°, treated with 18.4 g (0.13 mol) of methyl iodide over a period of 20 minutes and stirred at 60° C. for a further 5 hours in order to complete the reaction. The mixture is treated cautiously with 5 ml of methanol and subsequently with 100 ml of water, the organic phase is diluted with 100 ml of ether, washed with saturated sodium chloride solution and dried with sodium sulphate. After evaporation of the solvent, there remain behind 24 g of crude product which are fractionally distilled. There are thus obtained 13.5 g (62.5%) of olfactorily good 5-methoxy-4-methyl-3-undecene of boiling point 97°-98° C./12 Torr, $n_D^{20} = 1.4366$.

Odour: green, leaf-like, fatty.

IR: 1670, 1125, 1102, 1092, 942, 850 cm$^{-1}$;

MS: 198(M+, 3), 169(3), 113(100), 97(2), 81(9), 55(2), 41(3).

EXAMPLE 14

Analogously to Example 1, 20.0 g (0.11 mol) of 4-methyl-3-undecen-5-ol are converted into its alcoholate with sodium hydride in toluene and subsequently reacted with 14.2 g (0.13 mol) of ethyl bromide to give the ethyl ether. After analogous working-up and evaporation of the solvent, there remain behind 28.5 g of crude product which are fractionally distilled. There are thus obtained 14.4 g (62.2%) of olfactorily good 5-ethoxy-4-methyl-3-undecene of boiling point 104° C./12 Torr, $n_D^{20} = 1.4351$.

Odour: ethereal, bitterish, green slightly fruity.

IR: 1670, 1112, 1085, 1000, 850 cm$^{-1}$;

MS: 212(M+, 2), 183(3), 127(100), 99(10), 81(9), 69(3), 55(9), 43(15), 43(16).

EXAMPLE 15

Analogously to Example 1, 10.0 g (0.047 mol) of 4-methyl-3-tridecen-5-ol are converted into its alcoholate with sodium hydride in toluene and subsequently reacted with 8.50 g (0.060 mol) of methyl iodide to give the methyl ether. After analogous working-up and evaporation of the solvent, there remain behind 13.6 g of crude product which are fractionally distilled. There are thus obtained 5.5 g (51.8%) of olfactorily good 5-methoxy-4-methyl-3-tridecene of boiling point 114° C./12 Torr, $n_D^{20} = 1.4407$.

Odour: nutty, fatty, green, slightly woody.

IR 1670, 1130, 1095, 850 cm$^{-1}$;

MS: 226(M+, 2), 197(3), 157(2), 113(100), 81(5), 69(2), 55(3), 41(3).

EXAMPLE 16

Analogously to Example 1, 11.0 g (0.065 mol) of 2,6-dimethyl-1,6-nonadien-5-ol are converted into its alcoholate with sodium hydride in toluene and subsequently reacted with methyl iodide to give the methyl ether. After analogous working-up and evaporation of the solvent, there remain behind 26.9 g of crude product which are fractionally distilled. There are thus obtained 6.2 g (52.3%) of olfactorily good 5-methoxy-2,6 dimethyl-1,6-nonadiene of boiling point 83°-84° C./12 Torr, $n_D^{20} = 1.4458$.

Odour: green, berry-like, fruity.

IR 3062, 1650, 1155, 1099, 1065, 940, 881, 850 cm$^{-1}$;

MS: 182(M+, 1), 150(15), 126(6), 113(100), 96(4), 81(19), 55(6), 41(6).

EXAMPLE 17

Analogously to Example 1, 11.0 g (0.06 mol) of 4-methyl-3,8(Z)-undecadien-5-ol are converted into its alcoholate with sodium hydride in toluene and subsequently reacted with 10.7 g (0.075 mol) of methyl iodide to give the methyl ether. After analogous working-up and evaporation of the solvent, there remain behind 15.0 g of crude product which are fractionally distilled. There are thus obtained 6.2 g (52.4%) of olfactorily good 5-methoxy-4-methyl-3,8(Z)-undecadiene of boiling point 100° C./12 Torr, $n_D^{20} = 1.4472$.

Odour: green, leather-like, oily(cod-liver oil).

IR 1665, 1097, 1062, 940, 852, 720 cm$^{-1}$;

MS: 196(M+, 1), 167(6), 135(2), 113(100), 95(2), 85(4), 81(10), 69(3), 55(3), 41(6).

EXAMPLE 18

15.0 g (0.081 mol) of 4-methyl-3-undecen-5-ol and 17.6 g (0.244 mol) of ethyl vinyl ether are placed in a reaction vessel and treated with 0.1 ml of concentrated hydrochloric acid while stirring. The mixture warms slightly and is stirred at room temperature for 24 hours and then taken up in hexane. The hexane solution is washed neutral with aqueous sodium hydrogen carbonate solution and water and dried with sodium sulphate. After evaporation of the solvent, there remain behind 22.0 g of crude product which are fractionally distilled. There are thus obtained 13.7 g (65.6%) of olfactorily good 5-[1'-ethoxyethoxy]-4-methyl-3-undecene of boiling point 87°-89° C./0.06 Torr, $n_D^{20} = 1.4366$. The product exhibits in the gas chromatographical analysis a double peak in the ratio of 1:1 corresponding to the two asymmetric carbon atoms in the molecule.

Odour: fruity, green, fatty.

IR 1130, 1090, 1058, 1025, 1010, 850 cm$^{-1}$;

MS: 256 (M+, 1), 183(3), 171(19), 167(11), 111(2), 97(2), 83(3), 81(4), 73(100), 55(5), 45(18).

EXAMPLE 19

(A) Flowery base

|  | Parts by weight |
|---|---|
| Terpineol | 260 |
| Hydroxycitronellal | 220 |
| Cinnamic alcohol substitute | 120 |
| Phenylethyl alcohol | 100 |
| Cinnamyl formate | 20 |
| Linalool | 15 |
| Terpenyl acetate | 10 |
| Musk ketone | 10 |
| Geranyl acetate | 10 |
| Jasmine synthetic | 10 |
| Eugenol | 5 |
| Indole [10% in dipropylene glycol (DPG)] | 5 |
| Decanal (10% in DPG) | 5 |
| p-Methylacetophenone | 5 |
| Undecalactone | 5 |
|  | 800 |

By the addition of 200 parts of 5-methoxy-4-methyl-3-decene the original base surprisingly becomes much more fruity, the top of the novel base is greener and fresher and has a by far more powerful radiance than the top of the base without the addition.

(B) Perfumery base of the fougére type

|  | Parts by weight |
|---|---|
| Lavender oil | 200 |
| Amyl salicylate | 200 |
| Tree moss (50% in propylene glycol) | 80 |
| Citronellol | 80 |
| Geraniol | 80 |
| Musk ketone | 80 |

-continued

| | Parts by weight |
|---|---|
| Bergamot oil | 80 |
| α-Ionone | 80 |
| α-Hexylcinnamaldehyde | 30 |
| Eugenol | 20 |
| Metambrate TM GIV<br>(1-acetoxy-1-methyl-2-sec.butyl-cyclohexane) | 20 |
| | 950 |

If 50 parts of 5-methoxy-4-methyl-3-decene are added to this fougére base, then the base becomes much fresher and more spicy. It receives a by far more typical lavender-fougére note.

(C) Woody base

| | Parts by weight |
|---|---|
| Bergamot oil | 200 |
| Patchouli oil | 200 |
| Sandalwood oil | 200 |
| Cedryl acetate | 100 |
| Methyl dihydrojasmonate | 70 |
| Methylionone | 50 |
| P-Tert.butylcyclohexyl acetate | 50 |
| Basil oil | 30 |
| | 900 |

If 10 parts of 5-methoxy-2,6-dimethyl-6-nonene are added to the foregoing woody base, then there results a base with a completely new direction. The novel base is less herby-spicy, it points very strongly in the direction of chypre with a sweetish nuance and a character in the direction of gingerbread. Remarkably, this effect can be ascertained even after 24 hours. On the other hand, in the original base after this time the patchouli note appears sharply. After the addition, the base is, in comparison, softer and the patchouli note is advantageously enveloped.

(D) Green-flowery perfumery base

| | Parts by weight |
|---|---|
| Hydroxycitronellal | 130 |
| Bergamot oil | 130 |
| α-Ionone | 100 |
| α-Hexylcinnamaldehyde | 100 |
| Heliotropin | 70 |
| Styrallyl acetate | 80 |
| Ylang synthetic | 80 |
| Benzyl acetate | 80 |
| Phenylethyl alcohol | 80 |
| 2,6-Dimethylheptan-2-ol | 60 |
| Jasmine synthetic | 20 |
| Decalactone | 5 |
| | 935 |

If 65 parts of 5-methoxy-2,6-dimethyl-6-nonene are added to this base, then in the 24 hours value a very pleasant-flowery-cosmetic note of the original composition is underlined; this note is reminiscent of wallflower.

(E) Perfumery base (green flowery)

| | Parts by weight |
|---|---|
| Hydroxycitronellal | 130 |
| Bergamot oil | 130 |
| α-Ionone | 100 |
| α-Hexylcinnamaldehyde | 100 |
| Heliotropin | 70 |
| Styrallyl acetate | 80 |
| Ylang synthetic | 80 |
| Benzyl acetate | 80 |
| Phenylethyl alcohol | 80 |
| 2,6-Dimethylheptan-2-ol | 60 |
| Jasmine synthetic | 20 |
| Decalactone | 5 |
| | 935 |

By the addition of 65 parts of 5-[1'-ethoxyethoxy]-4-methyl-3-decene there is produced in this base an interesting green top note which at the same time is very pleasantly reminiscent of the scent of natural violets and is distinguished by a freshness not previously observable.

(F) Perfumery base of the chypre type

| | Parts by weight |
|---|---|
| Methyl 1-methylcyclododecyl ether | 200 |
| Bergamot oil | 150 |
| Hydroxycitronellal | 100 |
| Pine oil Pumillon | 80 |
| Citronellol | 80 |
| Petitgrain oil | 60 |
| Musk 174 TM GIV (12-oxahexadecanolide) | 60 |
| Coriander oil | 40 |
| Galbanum oil | 40 |
| Cedarwood oil | 40 |
| Patchouli oil | 40 |
| Lemon oil | 40 |
| Elemi oil | 10 |
| Oak moss decolourized | 20 |
| | 960 |

If 40 parts of 5-[1'-ethoxyethoxy]-4-methyl-3-decene are added to this chypre base, then it takes on a very pleasant fresh-fruity note which is reminiscent of citrus. Moreover, the base now has much more volume, i.e. the radiance of the novel composition is considerably greater.

(G) Base of the cologne type

| | Parts by weight |
|---|---|
| Myrascone TM GIV (2-ethyl-3,6,6-trimethyl-2-cyclohexene-1-carboxylic acid ethyl ester) | 80 |
| Bergamot oil | 80 |
| Galaxolide ® IFF (1,3,4,6,7,8-hexahydro-4,6,6,7,8,8-hexamethyl-cyclopenta-γ-2-benzopyran) | 60 |
| Hydroxycitronellal | 60 |
| Madrox TM GIV (1-methyl-1-methoxy-cyclododecane) | 60 |
| Bornyl acetate | 40 |
| Sandalore ® GIV [3-methyl-5-(2,2,3-trimethylcyclopent-3-en-1-yl)-pentan-2-ol] | 30 |
| Musk ketone | 40 |
| Givescone TM GIV (2-ethyl-6,6-dimethyl-2-cyclohexane-1-carboxylic acid ethyl ester) | 20 |
| Petitgrain oil | 20 |
| Corps Cassis TM GIV (p-menthane-8-thiol-3-one) | 5 |
| Tree moss absolute | 5 |
| Dipropylene glycol | 450 |
| | 950 |

The addition of 50 parts of 5-ethoxy-2,6-dimethyl-6-nonene brings about a very good intensification of the top note of the original cologne base, a spicy-herby-woody note being brought into prominence.

We claim:

1. A compound of the formula

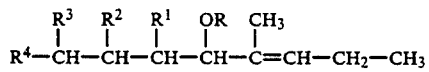

wherein:

R represents an alkyl group of one to four carbons, an alkenyl group of two to four carbons or a 1-alkoxyalkyl group of the formula

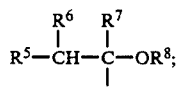

$R^1$, $R^2$ and $R^3$ may be the same or different and represent hydrogen, methyl or ethyl;

$R^4$ represents hydrogen, an alkyl group of from one to five carbons atoms, or an alkenyl group of from two to four carbon atoms;

$R^5$, $R^6$ and $R^7$ may be the same or different and represent hydrogen, methyl or ethyl with the proviso that the sum $R^5+R^6+R^7$ does not exceed two carbon atoms; and $R^8$ represents methyl or ethyl;

with the proviso that at least two, but not more than three of the symbols $R^1$, $R^2$, $R^3$ and $R^4$ represent hydrogen.

2. A compound according to claim 1 wherein
R represents methyl, ethyl or 1-ethoxyethyl
$R^1$ and $R^2$ represent hydrogen
$R^3$ represents hydrogen or methyl
$R^4$ represents methyl or ethyl.

3. A compound according to claim 1 selected from the group consisting of 5-methoxy-4,6-dimethyl-3-octene; 5-methoxy-4,6-dimethyl-3-nonene; 5-methoxy-4,7-dimethyl-3-nonene; 5-methoxy-4-methyl-3-undecene; 5-ethoxy-4-methyl-3-undecene; 5-methoxy-4-methyl-3-tridecene; 5-ethoxy-4-methyl-3-decene; 5-butoxy-4-methyl-3-decene; 5-allyloxy-4-methyl-3-decene; 5-(1'-methoxy-1'methyl-ethoxy)-4-methyl-3-decene; 5-(1'-methoxy-1'methyl-ethoxy)-2,6-dimethyl-6-nonene and 5-(1'-ethyoxy-ethoxy)-4-methyl-3-undecene.

4. A compound according to claim 1 identified as 5-methoxy-4-methyl-3-decene.

5. A compound according to claim 1 identified as 5-methoxy-2,6-dimethyl-6-nonene.

6. A compound according to claim 1 identified as 5-ethoxy-2,6-dimethyl-6-nonene.

7. A compound according to claim 1 identified as 5-(1'-ethoxyethoxy)-4-methyl-3-decene.

8. A compound according to claim 1 identified as 5-(1'ethoxyethoxy)-2,6-dimethyl-6-nonene.

9. An odorant and/or flavoring composition comprising an effective amount of a compound of the formula:

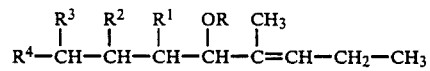

wherein:

R represents an alkyl group of one to four carbons, an alkenyl group of two to four carbons or a 1-alkoxyalkyl group of the formula

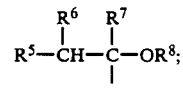

$R^1$, $R^2$ and $R^3$ may be the same of different and represent hydrogen, methyl or ethyl;

$R^4$ represents hydrogen, an alkyl group of from one to five carbon atoms, or an alkenyl group of from two to four carbon atoms;

$R^5$, $R^6$ and $R^7$ may be the same or different and represent hydrogen, methyl or ethyl with the proviso that the sum $R^5+R^6+R^7$ does not exceed two carbon atoms; and $R^8$ represents methyl or ethyl;

with the proviso that at least two, but not more than three of the symbols $R^1$, $R^2$, $R^3$ and $R^4$ represent hydrogen; and at least one other olfactory agent.

10. A composition according to claim 9 wherein
R represents methyl, ethyl or 1-ethoxyethyl
$R^1$ and $R^2$ represent hydrogen
$R^3$ represents hydrogen or methyl
$R^4$ represents methyl or ethyl.

11. A composition according to claim 9 wherein there is present at least one of the compounds selected from the group consisting of 5-methoxy-4,6-dimethyl-3-octene; 5-methoxy-4,6-dimethyl-3-nonene; 5-methoxy-4,7-dimethyl-3-nonene; 5-methoxy-4-methyl-3-undecene; 5-ethoxy-4-methyl-3-undecene; 5-methoxy-4-methyl-3-tridecene; 5-ethoxy-4-methyl-3-decene; 5-butoxy-4-methyl-3-decene; 5-allyloxy-4-methyl-3-decene; 5-(1'-methoxy-1'methyl-ethoxy)-4-methyl-3-decene; 5-(1'-methoxy-1'methyl-ethoxy)-2,6-dimethyl-6-nonene and 5-(1'-ethoxy-ethoxy)-4-methyl-3-undecene.

12. A composition according to claim 9 containing 5-methoxy-4-methyl-3-decene.

13. A composition according to claim 9 containing 5-methoxy-2,6-dimethyl-6-nonene.

14. A composition according to claim 9 containing 5-ethoxy-2,6-dimethyl-6-nonene.

15. A composition according to claim 9 containing 5-(1'-ethoxy-ethoxy)-4-methyl-3-decene.

16. A composition according to claim 9 containing 5-(1'-ethoxyethoxy)-2,6-dimethyl-6-nonene.

17. A method for improving the olfactory properties of odorant and/or flavor compositions which comprises adding thereto an effective amount of a compound of the formula:

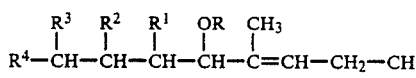

wherein:

R represents an alkyl group of one to four carbons, an alkenyl group of two to four carbons or a 1-alkoxyalkyl group of the formula

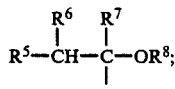

$R^1$, $R^2$ and $R^3$ may be the same or different and represent hydrogen, methyl or ethyl;

$R^4$ represents hydrogen, an alkyl group of from one to five carbon atoms, or an alkenyl group of from two to four carbon atoms;

$R^5$, $R^6$ and $R^7$ may be the same or different and represent hydrogen, methyl or ethyl with the proviso that the sum $R^5+R^6+R^7$ does not exceed two carbon atoms; and $R^8$ represents methyl or ethyl;

with the proviso that at least two, but not more than three of the symbols $R^1$, $R^2$, $R^3$ and $R^4$ represent hydrogen.

18. A method according to claim 17 wherein there is added at least one of the compounds selected from the group consisting of 5-methoxy-4,6-dimethyl-3-octene; 5-methoxy-4,6-dimethyl-3-nonene; 5-methoxy-4,7-dimethyl-3-nonene; 5-methoxy-4-methyl-3-undecene; 5-ethoxy-4-methyl-3-undecene; 5-methoxy-4-methyl-3-tridecene; 5-ethoxy-4-methyl-3-decene; 5-butoxy-4-methyl-3-decene; 5-allyloxy-4-methyl-3-decene; 5-(1'-methoxy-1'methyl-ethoxy)-4-methyl-3-decene; 5-(1'-methoxy-1'methyl-ethoxy)-2,6-dimethyl-6-nonene and 5-(1'-ethoxyethoxy)-4-methyl-3-undecene.

19. A method according to claim 17 wherein there is added 5-methoxy-4-methyl-3-decene.

20. A method according to claim 17 wherein there is added 5-methoxy-2,6-dimethyl-6-nonene.

21. A method according to claim 17 wherein there is added 5-ethoxy-2,6-dimethyl-6-nonene.

22. A method according to claim 17 wherein there is added 5-(1'-ethoxyethoxy)-4-methyl-3-decene.

23. A method according to claim 17 wherein there is added 5-(1'-ethoxyethoxy)-2,6-dimethyl-6-nonene.

24. A compound of the formula:

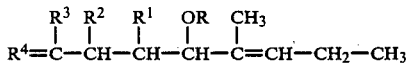

wherein:

R represents an alkyl group of one to four carbons, an alkenyl group of two to four carbons or a 1-alkoxyalkyl group of the formula

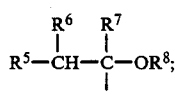

$R^1$, $R^2$ and $R^3$ may be the same or different and represent hydrogen, methyl or ethyl;

$R^4$ represents an alkylidene group of from one to four carbon atoms;

$R^5$, $R^6$ and $R^7$ may be the same of different and represent hydrogen, methyl or ethyl with the proviso that the sum $R^5+R^6+R^7$ does not exceed two carbon atoms; and $R^8$ represents methyl or ethyl;

with the proviso that at least two of the symbols $R^1$, $R^2$ and $R^3$ represent hydrogen.

25. A compound according to claim 24 selected from the group consisting of 5-methoxy-2,6-dimethyl-1,6-nonadiene and 5-methoxy-4-methyl-3,8-(Z)-undecadiene.

26. An odorant and/or flavoring composition comprising an effective amount of a compound of the formula:

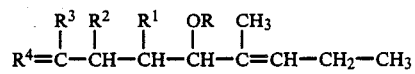

wherein:

R represents an alkyl group of one to four carbons, an alkenyl group of two to four carbons or a 1-alkoxyalkyl group of the formula

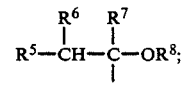

$R^1$, $R^2$ and $R^3$ may be the same or different and represent hydrogen, methyl or ethyl;

$R^4$ represents an alkylidene group of from one to four carbon atoms;

$R^5$, $R^6$ and $R^7$ may be the same or different and represent hydrogen, methyl or ethyl with the proviso that the sum $R^5+R^6+R^7$ does not exceed two carbon atoms; and $R^8$ represents methyl or ethyl;

with the proviso that at least two of the symbols $R^1$, $R^2$ and $R^3$ represent hydrogen; and at least one other olfactory agent.

27. A composition according to claim 26 wherein there is present at least one of the compounds selected from the group consisting of 5-methoxy-2,6-dimethyl-1,6-nonadiene and 5-methoxy-4-methyl-3,8-(Z)-undecadiene.

28. A method for improving the olfactory properties of odorant and/or flavor compositions which comprises adding thereto an effective amount of a compound of the formula:

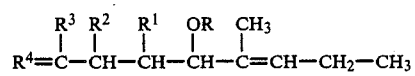

wherein:

R represents an alkyl group of one to four carbons, an alkenyl group of two to four carbons or a 1-alkoxyalkyl group of the formula

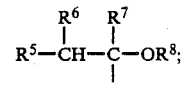

$R^1$, $R^2$ and $R^3$ may be the same or different and represent hydrogen, methyl or ethyl;

$R^4$ represents an alkylidene group of from one to four carbon atoms;

$R^5$, $R^6$ and $R^7$ may be the same or different and represent hydrogen, methyl or ethyl with the proviso that the sum $R^5+R^6+R^7$ does not exceed two carbon atoms; and $R^8$ represents methyl or ethyl;

with the proviso that at least two of the symbols $R^1$, $R^2$ and $R^3$ represent hydrogen.

29. A method according to claim 28 wherein there is added at least one of the compounds selected from the group consisting of 5-methoxy-2,6-dimethyl-1,6-nonadiene and 5-methoxy-4-methyl-3,8-(Z)-undecadiene.

* * * * *